US012673198B2

(12) United States Patent
Long et al.

(10) Patent No.: US 12,673,198 B2
(45) Date of Patent: Jul. 7, 2026

(54) WOUND THERAPY SYSTEM AND WOUND DRESSING WITH PH SENSOR

(71) Applicant: KCI Licensing, Inc., San Antonio, TX (US)

(72) Inventors: Justin Alexander Long, Lago Vista, TX (US); Konstantinos Petropoulos, San Antonio, TX (US); Silvia Generelli, San Antonio, TX (US); Christopher Brian Locke, Bournemouth (GB)

(73) Assignee: KCI Licensing Inc., San Antonio, TX (US)

( * ) Notice: Subject to any disclaimer, the term of this patent is extended or adjusted under 35 U.S.C. 154(b) by 236 days.

(21) Appl. No.: 17/769,603

(22) PCT Filed: Oct. 15, 2020

(86) PCT No.: PCT/IB2020/059721
§ 371 (c)(1),
(2) Date: Apr. 15, 2022

(87) PCT Pub. No.: WO2021/074856
PCT Pub. Date: Apr. 22, 2021

(65) Prior Publication Data
US 2024/0130898 A1      Apr. 25, 2024
US 2024/0226537 A9      Jul. 11, 2024

Related U.S. Application Data

(60) Provisional application No. 62/923,293, filed on Oct. 18, 2019.

(51) Int. Cl.
*A61N 1/04*        (2006.01)
*A61F 13/00*       (2024.01)
(Continued)

(52) U.S. Cl.
CPC ............ *A61N 1/0468* (2013.01); *A61F 13/05* (2024.01); *A61M 1/73* (2021.05); *A61M 1/91* (2021.05);
(Continued)

(58) Field of Classification Search
CPC ................... A61N 1/0468; A61F 13/05; A61F 2013/00948; A61F 13/00055; A61M 1/73;
(Continued)

(56) References Cited

U.S. PATENT DOCUMENTS 1,355,846  A      10/1920  Rannells
2,547,758  A       4/1951  Keeling
(Continued)

FOREIGN PATENT DOCUMENTS

AU          550575  B2      3/1986
AU          745271  B2      3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Catharine L Anderson
*Assistant Examiner* — Seth Han

(57)                ABSTRACT

A wound therapy system having a wound dressing for treating a wound includes a sensor that measures a pH level at a wound area. The sensor has a circuit that includes a first electrode and one or more second electrodes. The first electrode has a changeable conductivity that changes according to a hydrogen ion concentration level. The one or more second electrodes are configured with a fixed conductivity that does not change with the hydrogen ion concen-
(Continued)

100 tration level. The first electrode is coated with a porous protective membrane formed from a sulfonated and/or carboxylated copolymer.

19 Claims, 4 Drawing Sheets

(51) Int. Cl.
| | |
|---|---|
| *A61F 13/05* | (2024.01) |
| *A61M 1/00* | (2006.01) |
| A61B 5/145 | (2006.01) |

(52) U.S. Cl.
CPC ......... *A61M 1/966* (2021.05); *A61B 5/14539* (2013.01); *A61B 2562/125* (2013.01); *A61F 2013/00948* (2013.01); *A61M 1/915* (2021.05); *A61M 2205/3317* (2013.01)

(58) Field of Classification Search
CPC .................... A61M 1/91; A61M 1/966; A61M 2205/3324; A61B 5/14539; A61B 5/6834
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,653,499 A * | 3/1987 | Murray, Jr. ........ | G01N 27/3335 600/348 |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,573,798 A * | 11/1996 | Kato ................... | G01N 27/333 427/523 |
| 5,607,388 A | 3/1997 | Ewall | |
| 5,636,643 A | 6/1997 | Argenta et al. | |
| 5,645,081 A | 7/1997 | Argenta et al. | |
| 6,023,630 A * | 2/2000 | Bacchi ............... | A61B 5/14539 600/348 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0045309 A1 * | 2/2010 | Zou ........................ | A61B 5/073 324/663 |

(56) References Cited

U.S. PATENT DOCUMENTS

| | | | |
|---|---|---|---|
| 2014/0163491 A1 | 6/2014 | Schuessler et al. | |
| 2015/0080788 A1 | 3/2015 | Blott et al. | |
| 2015/0126834 A1* | 5/2015 | Wang | B32B 38/10 |
| | | | 156/247 |
| 2017/0261461 A1* | 9/2017 | Bychkova | H01M 4/02 |
| 2018/0372701 A1* | 12/2018 | Molter | H01M 8/04992 |
| 2019/0076298 A1* | 3/2019 | Quintanar | A61M 1/95 |

FOREIGN PATENT DOCUMENTS

| | | |
|---|---|---|
| AU | 755496 B2 | 12/2002 |
| CA | 2005436 A1 | 6/1990 |
| DE | 2640413 A1 | 3/1978 |
| DE | 4306478 A1 | 9/1994 |
| DE | 29504378 U1 | 9/1995 |
| EP | 0100148 A1 | 2/1984 |
| EP | 0117632 A2 | 9/1984 |
| EP | 161865 A2 | 11/1985 |
| EP | 358302 A2 | 3/1990 |
| EP | 1018967 A1 | 7/2000 |
| GB | 692578 A | 6/1953 |
| GB | 2195255 A | 4/1988 |
| GB | 2197789 A | 6/1988 |
| GB | 2220357 A | 1/1990 |
| GB | 2235877 A | 3/1991 |
| GB | 2329127 A | 3/1999 |
| GB | 2333965 A | 8/1999 |
| JP | 4129536 B2 | 8/2008 |
| SG | 71559 | 4/2002 |
| WO | 80/02182 A1 | 10/1980 |
| WO | 8704626 A1 | 8/1987 |
| WO | 90010424 A1 | 9/1990 |
| WO | 93009727 A1 | 5/1993 |
| WO | 94020041 A1 | 9/1994 |
| WO | 9605873 A1 | 2/1996 |
| WO | 97/18007 A1 | 5/1997 |
| WO | 99/13793 A1 | 3/1999 |
| WO | 2019/063481 A1 | 4/2019 |
| WO | 2019/140444 A1 | 7/2019 |

OTHER PUBLICATIONS

Chariker, Mark E., M.D., et al; "Effective Management of incisional and cutaneous fistulae with closed suction wound drainage"; Contemporary Surgery, vol. 34, Jun. 1989, pp. 59-63.

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A.C.® Therapy Clinical Guidelines: A Reference Source for Clinicians; Jul. 2007.

International Search Report and Written Opinion Corresponding to Application No. PCT/IB2020/059721, mailed Feb. 22, 2021.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

* cited by examiner

WOUND THERAPY SYSTEM AND WOUND DRESSING WITH PH SENSOR

CROSS-REFERENCE TO RELATED APPLICATIONS

This application claims the benefit of priority to U.S. Provisional Application No. 62/923,293, filed on Oct. 18, 2019, which is incorporated herein by reference in its entirety.

BACKGROUND

Clinicians approach wound care through various treatment approaches. One way that clinicians determine the stage of a wound or the regression or progression of wounds is through a surrogate value known as pH. pH is a measure of the decimal logarithm of the reciprocal of the local hydrogen ion activity within a wound or wound exudate. In other words it is an indicator of the acidity or alkalinity of a wound or wound exudate. The impact of pH in wound care has shown that if a wound is inflamed, the pH may be in an acidic level (e.g., pH level is 4-6.5). Increased microbial growth may occur when the pH is within the acidic level. If a wound is chronic, the pH may be in an alkaline level (e.g., pH level is 8.0 or greater). Optimum protease activity and cellular migration may occurs when the pH level is around pH 7. Thus, optimum acute healing may occur when the pH level is around pH 7. Therefore, measuring a pH level at a wound area helps stage or even predict potential wound healing or lack of healing outcomes.

SUMMARY

One implementation of the present disclosure is a sensor for measuring a pH level in a wound therapy system for treating multiple zones of a wound that includes a circuit configured to measure a pH level at a wound area. The circuit includes a first electrode and one or more second electrodes. The first electrode is configured with a changeable or variable conductivity that changes according to a hydrogen ion concentration level. The one or more second electrodes are configured with a fixed conductivity that does not change with the hydrogen ion concentration level.

Another implementation of the present disclosure is a wound therapy system having a sensor for measuring a pH level at a wound area. The sensor includes a first electrode and one or more second electrodes. The first electrode is configured with a changeable or variable conductivity that changes according to a hydrogen ion concentration level. The one or more second electrodes are configured with a fixed conductivity that does not change with the hydrogen ion concentration level.

Another implementation of the present disclosure is a method of fabricating a sensor for measuring a pH level at a wound area. The method includes: screen-printing a first electrode at a first end of a substrate; depositing iridium oxide on the first electrode; depositing porous protective membrane coating on the first electrode; and screen-printing one or more second electrode at the first end of the substrate. The first electrode has changeable or variable conductivity that changes according to a hydrogen ion concentration level. The one or more second electrodes has fixed conductivity that does not change according to a hydrogen ion concentration level.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Figure 1A:
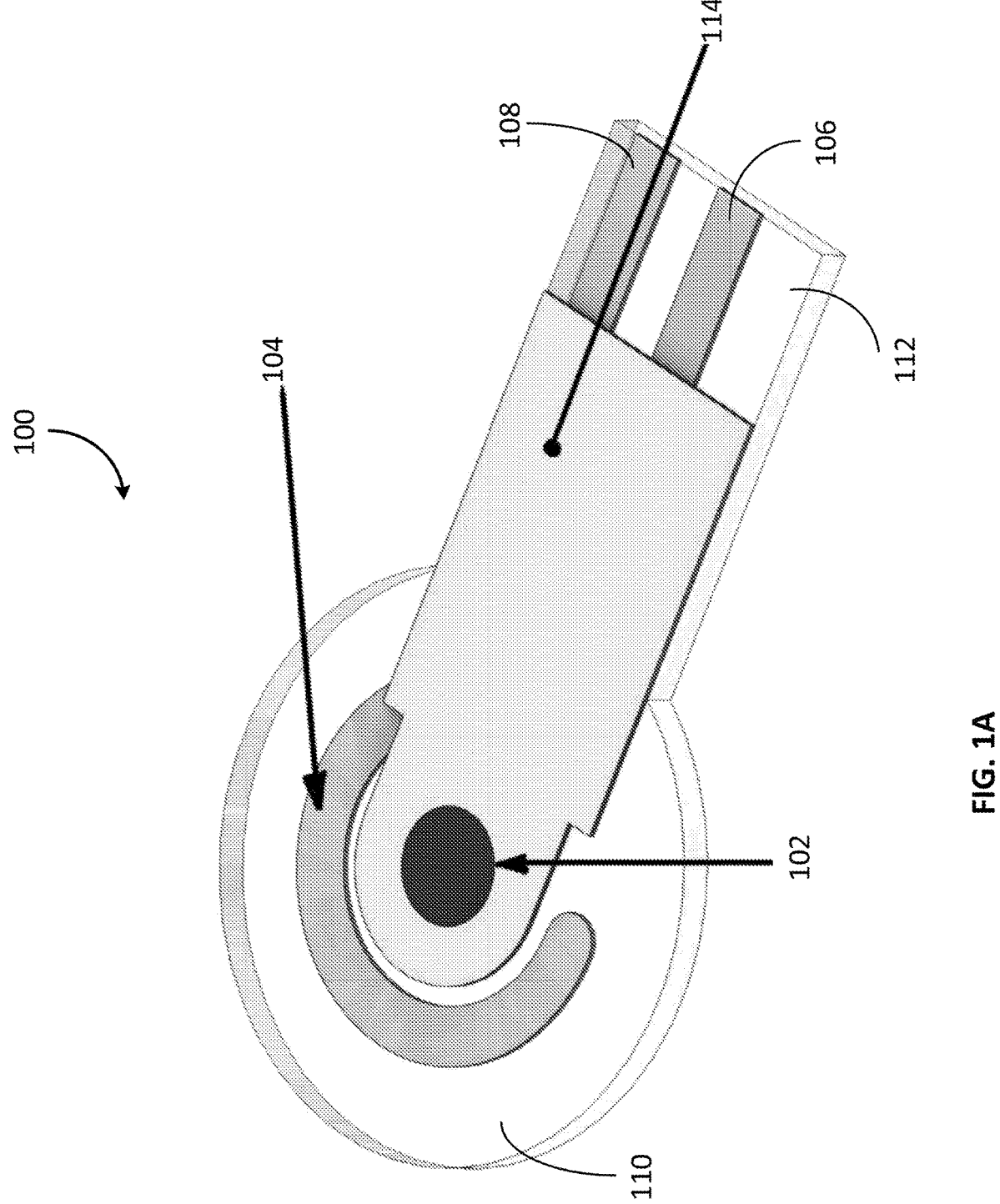
FIG. 1A is a diagram of a top perspective view of a sensor 100 according to an illustrative embodiment.
Figure 1B:
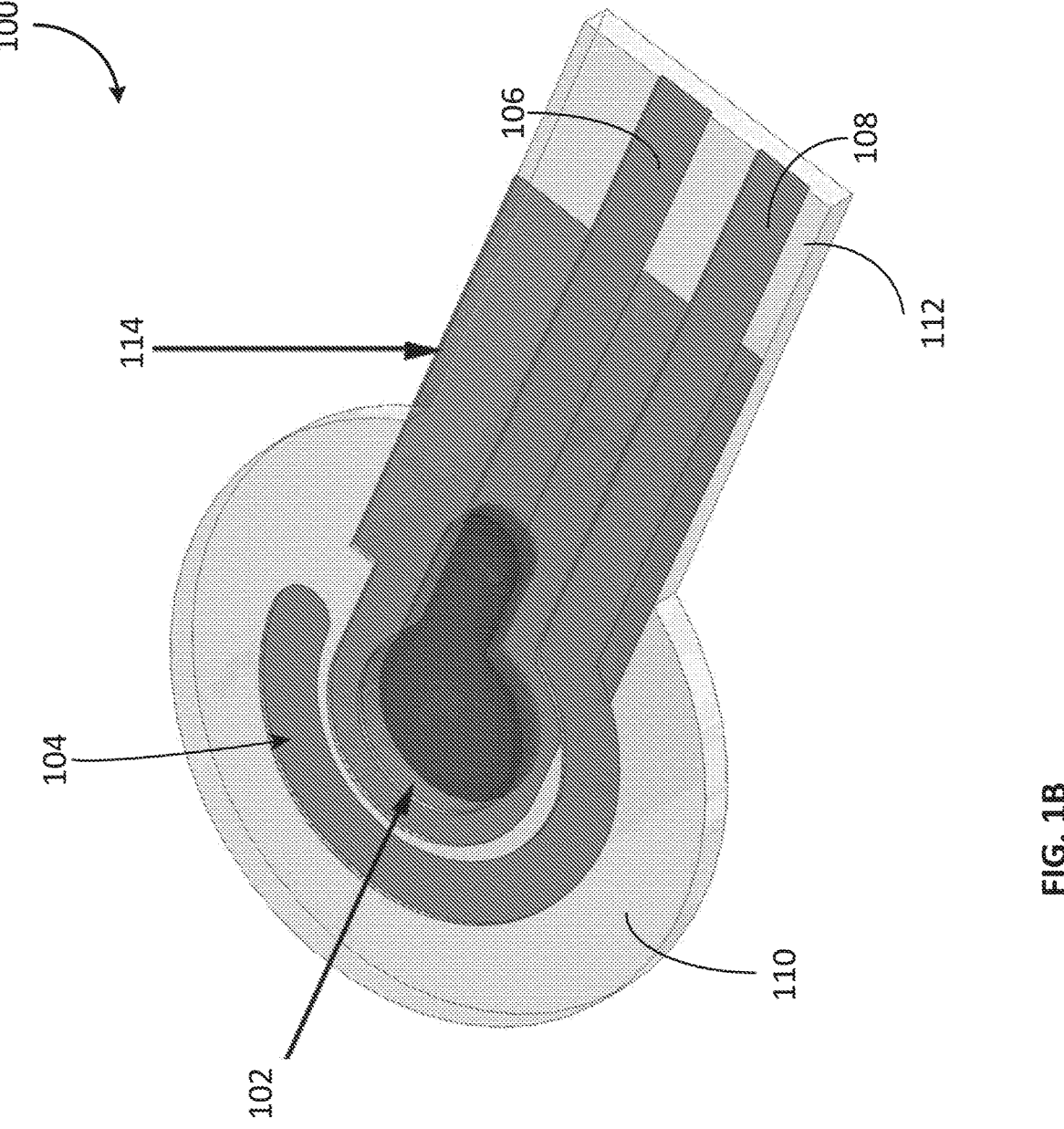
FIG. 1B is a diagram of a bottom perspective view of the sensor 100 of FIG. 1 according to an illustrative embodiment.

Referring to FIG. 1A and FIG. 1B, a diagram of a sensor 100 for measuring a pH level at a wound area is shown according to an illustrative embodiment. FIG. 1A shows a top view of the sensor 100 and FIG. 1B shows a bottom view of the sensor 100. The sensor 100 can be used in a wound therapy system for measuring a pH level at a wound area. The sensor 100 can be used in various chemical and/or biochemical environments. The sensor 100 includes a substrate 112, and a first electrode 102, a second electrode 104, a third electrode 106, and a fourth electrode 108 printed on the substrate 112.

The first electrode 102 is screen-printed on a first end of the substrate 112. The first end of the substrate 112 is disposed at a wound area to contact with wound fluid when the sensor 100 is in use for a wound therapy system. The first electrode 102 is used for directly contacting wound fluid at the wound area. The first electrode 102 is printed with a carbon-based ink or paste. In some embodiments, the first electrode 102 may be printed using any suitable materials. The first electrode 102 has a circular shape with a predetermined diameter (e.g., approximately 1mm) according to some embodiments.

The first electrode 102 is formed with metal oxide electrodeposition of iridium oxide on top of the carbon-based ink or paste. The metal oxide electrodeposition of iridium oxide enables the first electrode 102 with a changeable conductivity according to a hydrogen ion concentration. Measuring the changed conductivity of the first electrode 102 can be used for indicating a change of pH level. When the hydrogen ion concentration at the first electrode 102 increases, the pH level decreases and the conductivity of the first electrode 102 increases. When the hydrogen ion concentration at the first electrode 102 decreases, the pH level increases and the conductivity of the first electrode 102 decreases. In some embodiments, the first electrode 102 can be deposited with any suitable material that allows the conductivity of the first electrode 102 change along with a hydrogen ion concentration level. In some applications, it is believed that direct contact between the wound fluid and the iridium oxide material of the electrode may inhibit the proper operation of the electrode. It would be desirable to provide a coating layer on the electrode that permits ion passage from the wound fluid to the electrode for proper pH determination, while preventing direct contact between the fluid and the electrode in order to protect the electrode.

According to the illustrated embodiment, the first electrode 102 is coated with a porous protective membrane coating to protect the first electrode 102 from the protein rich, enzyme rich, and/or oxidizing wound environments. In some embodiments, the porous protective membrane coating includes a sulfonated and/or carboxylated copolymer, such as a sulfonated tetrafluoroethylene based fluoropolymer-copolymer. A particular example of a sulfonated and/or carboxylated copolymer suitable for the present technology is a copolymer of tetrafluoroethylene with 2-[1-[difluoro-[(trifluoroethenyl)oxy]methyl]-1,2,2,2-tetrafluoroethoxy]-1, 1,2,2,-tetrafluoro-ethanesulfonyl fluoride (also referred to as tetrafluoroethylene-perfluoro-3,6-dioxa-4-methyl-7-octene-sulfonic acid copolymer). Suitable a sulfonated and/or carboxylated copolymers may be commercially obtained from a variety of sources, and includes (but is not limited to) copolymers utilized for ion exchange membranes and products under the tradename Nafion®. The porous protective membrane is intended to protect the electrode from the deleterious effects of the wound environment, while remaining sufficiently porous to permit ion transfer for determining pH of the wound fluid. According to one embodiment, the porous protective membrane coating comprises a layer of sulfonated and/or carboxylated copolymer disposed over the iridium oxide layer of the electrode. The layer of sulfonated and/or carboxylated copolymer may be formed on the electrode by depositing a solution of the sulfonated and/or carboxylated copolymer on the electrode, where such solutions further include one or more solvents. Such solvents include an organic solvent, water, or both. Exemplary organic solvents include dimethyl ether, diethyl ether, methylene chloride, chloroform, acetone, ethyl acetate, or a combination of any two or more thereof. By way of example of such depositing, an aqueous solution including 5% by weight of tetrafluoroethylene-perfluoro-3,6-dioxa-4-methyl-7-octenesulfonic acid copolymer may be applied to the iridium oxide layer and thereafter the solvent of the aqueous solution removed (e.g., by evaporation). The layer may therefore be formed from solutions including a sulfonated and/or carboxylated copolymer where the sulfonated and/or carboxylated copolymer is included in a concentration, for example, within a range from 5% to 4% by weight of the solution, or within a range from 4% to 3% by weight of the solution, or within a range from 3% to 2% by weight of the solution, or within a range from 2% to 1% by weight of the solution, or within a range from 5% to 6% by weight of the solution, or within a range from 6% to 7% by weight of the solution, or within a range from 7% to 8% by weight of the solution, or within a range from 8% to 9% by weight of the solution, all of which are included within the scope of this disclosure. In some embodiments, the porous protective membrane coating specifically excludes certain materials, such as chitosan, in any concentration, and more particularly excludes chitosan in a concentration of 0.1%-2.5%.

The second electrode 104 is screen-printed on the first end of the substrate 112. In some embodiments, the second electrode 104 includes one or more electrodes. The second electrode 104 is used as a reference electrode with a fixed conductivity. The fixed conductivity of the second electrode 104 does not change along with a change of a hydrogen ion concentration level or a change of pH level. The second electrode 104 is printed with silver chloride paste or ink to provide a better conductivity compared to the first electrode 102. In some embodiments, the second electrode 104 can be printed with any suitable material that allows the second electrode 104 have a fixed conductivity. The second electrode 104 is formed with a shape that is intended to at least partially surround the first electrode 102. The second electrode 104 is disposed in proximity to the first electrode 102.

The third electrode 106 is screen-printed on a second end of the substrate 112. The second end of the substrate 112 is an opposite end to the first end of the substrate 112. In some embodiments, the second end of the substrate 112 does not contact with wound fluid. The third electrode 106 is printed with silver chloride paste or ink. In some embodiments, the third electrode 106 can be printed with any suitable material that allows the third electrode 106 to have a fixed conductivity. The third electrode 106 is used as an electrical contact for voltage measurement. The third electrode 106 is electrically connected to the first electrode 102 via a first electrical trace (not shown).

The fourth electrode 108 is screen-printed on the second end of the substrate 112. In some embodiments, the fourth electrode 108 may include one or more electrodes. The fourth electrode 108 is printed with silver chloride paste or ink. In some embodiments, the fourth electrode 108 can be printed with any suitable material that allows the fourth electrode 108 to have a fixed conductivity. The fourth electrode 108 is used as an electrical contact for voltage measurement. The fourth electrode 106 is electrically connected to the second electrode 104 via a second electrical trace (not shown).

The substrate 112 is made of any suitable material that is bendable, non-stretchable, resistant to tensile and compressive forces, resistant to chemical degradation, and resistant to rapid oxidation. In some embodiments, the substrate 112 is made of polymeric material (e.g., 125 um polymeric film). In some embodiments, the first, second, third, and fourth electrodes 102, 104, 106, and 108 are all printed on the same side of the substrate 112.

The first end of the substrate 112 includes a sealing portion 110 that is formed on the periphery of the first end of the substrate 112. The sealing portion 110 is made of any suitable adhesive material that can seal the first end of the substrate to one or more components of the wound therapy system (e.g., a wound healing pad).

The substrate 112 is coated with an isolation ink layer 114 that separates and protects the printed electrodes (e.g., first, second, third, and fourth electrodes). The isolation ink layer 114 is applied such that only the first electrode 102 and the second electrode 104 are exposed to the wound fluid. In some embodiments, the isolation ink layer 114 includes a cyan screen printed ink.

Figure 2:
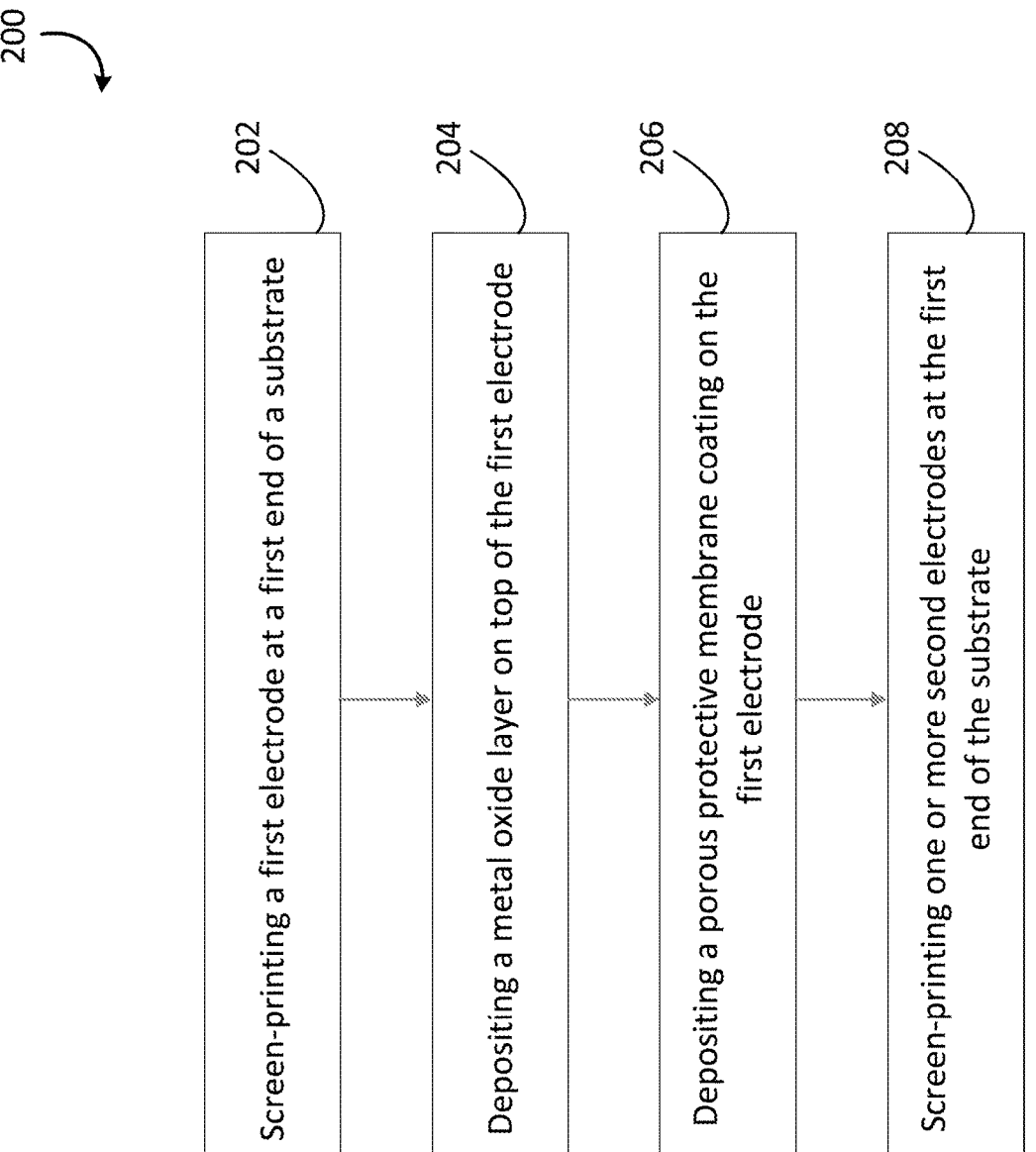
FIG. 2 is a flow diagram of fabricating a sensor for measuring a pH level at a wound area according to an illustrative embodiment.
Figure 3:
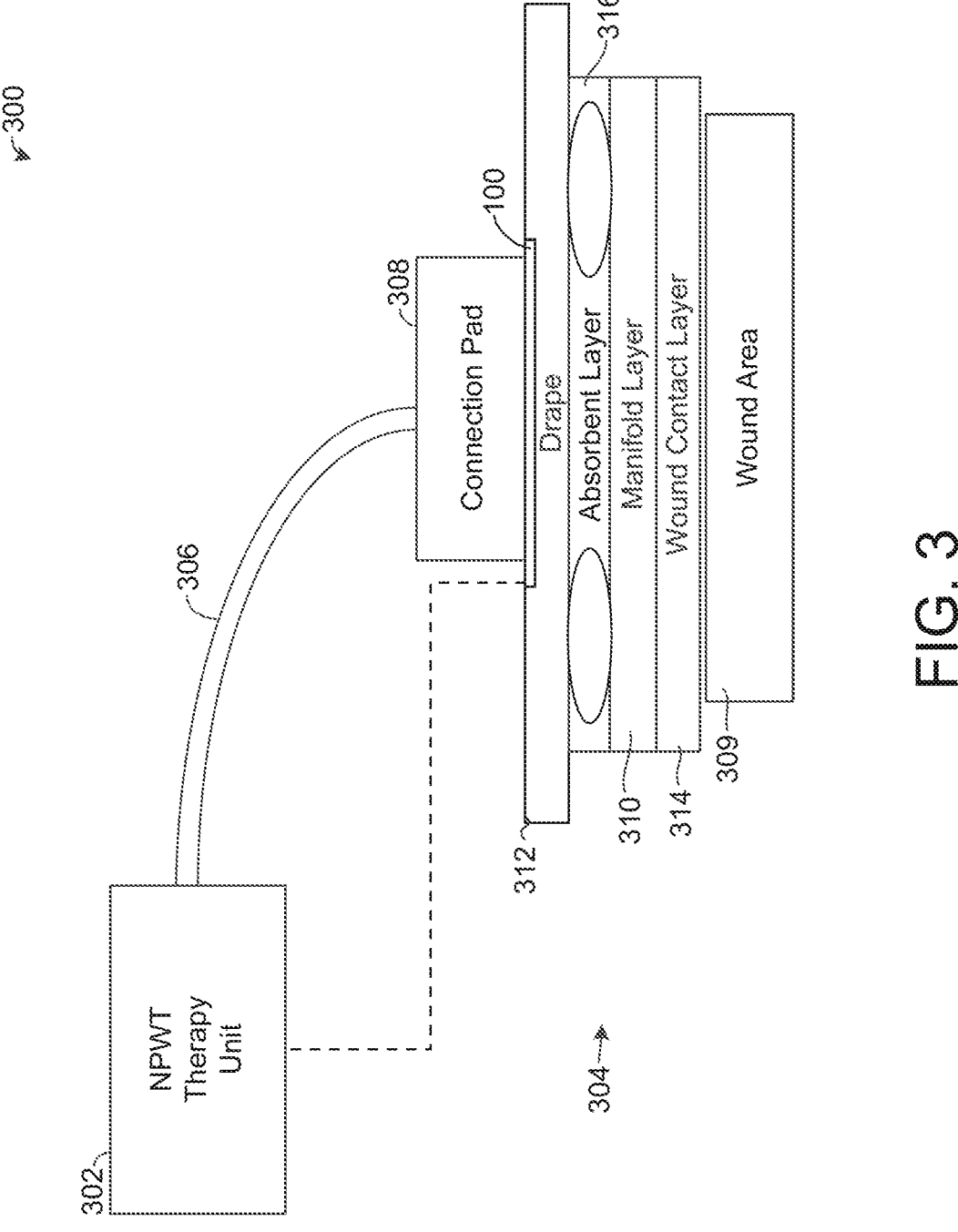
FIG. 3 is a schematic diagram of a wound therapy system with wound dressing having the sensor of FIGS. 1A-1B, according to an illustrative embodiment.

Referring to FIG. 2, a flow diagram of fabricating a sensor for measuring a pH level at a wound area is shown according to an illustrative embodiment. At step 202, a first electrode is screen-printed at a first end of a substrate. The first electrode is printed with a carbon-based ink or paste. In some embodiments, the first electrode may be printed using any suitable material.

At step 204, a metal oxide layer (e.g., iridium oxide) is deposited on top of the carbon-based ink or paste of the first electrode. The metal oxide electrodeposition enables the first electrode with a changeable conductivity according to a hydrogen ion concentration. In some embodiments, the first electrode can be deposited with any suitable material that allows the conductivity of the first electrode change along with a hydrogen ion concentration level. The metal oxide layer is dried at a desired temperature.

At step 206, a porous protective membrane coating is deposited on the first electrode. The porous protective membrane coating protects the first electrode from the protein rich, enzyme rich, and/or oxidizing wound environments. The porous protective membrane coating is deposited on top of the iridium oxide layer and is formed from a layer of the sulfonated and/or carboxylated copolymer. An aqueous solution comprising approximately 5% (by weight of the solution) sulfonated and/or carboxylated copolymer is deposited on the electrode and then evaporated to form the protective layer. In other embodiments, the solution deposited on the electrode to form the protective layer may comprise the sulfonated and/or carboxylated copolymer in other concentrations, such as within a range from 5% to 4% by weight of the solution, or within a range from 4% to 3% by weight of the solution, or within a range from 3% to 2% by weight of the solution, or within a range from 2% to 1% by weight of the solution, or within a range from 5% to 6% by weight of the solution, or within a range from 6% to 7% by weight of the solution, or within a range from 7% to 8% by weight of the solution, or within a range from 8% to 9% by weight of the solution, all of which are included within the scope of this disclosure. The porous protective membrane coating according to the present embodiment specifically excludes certain materials, such as chitosan. The sulfonated and/or carboxylated copolymer and water-based solution may be deposited on the iridium layer of the electrode using a controlled deposition process (for example a pipet tip or other suitable deposition device) until the first (i.e. working) electrode is covered. The sulfonated and/or carboxylated copolymer and water-based solution may be allowed to self-level on the first electrode until the solution uniformly covers the working electrode. Once the first electrode is uniformly covered then the solution is allowed cure or dry by evaporation at room temperature (for example approximately 20° C.) under a vent hood. A relatively high airflow at room temperature is intended to allow the coating layer to remain somewhat flexible during the drying process and to minimize or prevent the formation of microcracks or other imperfections that could compromise the sulfonated and/or carboxylated copolymerprotective layer.

At step 208, one or more second electrodes are screen-printed at the first end of the substrate. The one or more second electrodes are printed with a material that allows the one or more second electrodes have a fixed conductivity. The fixed conductivity does not change along with a change of a hydrogen ion concentration level or a change of pH level. The one or more second electrodes are printed with silver chloride paste or ink to provide a better conductivity compared to the first electrode. The one or more second electrodes are formed with a shape that is intended to at least partially surround the first electrode. The one or more second electrodes are disposed in close proximity to the first electrode.

According to any embodiment, the sensor 100 for measuring a pH level at a wound site, as shown and described herein, may be incorporated into a wound therapy system 300 having a wound care dressing 304 for use on a patient. The wound care dressing may 304 include negative pressure wound therapy (NPWT). In a NPWT application, the wound care dressing 304 may include any suitable construction and components intended for treatment of a particular wound type. According to one embodiment, the wound care dressing 304 includes a wound interface or contact layer 314 configured to overlie the wound and periwound area 309 of the patent. The wound interface layer 314 may be formed from a fenestrated film, such as a polyurethane film. A wound fluid manifold layer 310 may be provided above the wound interface layer 314. The manifold layer 310 may be formed from a porous hydrophobic foam material, such as GRANUFOAM™ by KCI Licensing, Inc., which is intended to permit and distribute flow of air and wound fluid or exudate from the wound area 309. An absorbent layer 316 may be provided over the manifold layer 310, and may comprise a superabsorbent polymer (SAP) material. The SAP is constructed of a superabsorbent powder, an acetate and ethylene copolymer, and a fiber material. In some embodiments, the superabsorbent powder is a sodium polyacrylate, such as Favor®-PAC320. In some embodiments, the acetate is a glue vinyl acetate, and the acetate and ethylene copolymer may be Pafra 8667. In some embodiments, the fiber material is a 65% viscose and 35% polyethylene terephthalate (PET) spunlace, such as LIDRO 50 g/m2. A drape layer 312 is disposed above the absorbent layer 316 and is formed from a high MVTR film, such as a thin layer of polyurethane film. One example of a suitable material for the drape layer is the polyurethane film known as ESTANE 5714F.

A negative pressure therapy unit 302, such as a V.A.C.U-LTA™ Therapy Unit by KCI Licensing, Inc. may be connected to the wound dressing 304 by suitable tubing 306. The tubing 306 may be connected to the drape layer 312 by a tubing connector pad 308, such as a SENSAT.R.A.C. connector by KCI Licensing, Inc. The sensor 100 for measuring a pH level at a wound site may be coupled at, or proximate to, the tubing connector pad in fluid communication with the wound exudate within the dressing. Sensor 100 may communicate with the therapy unit 302 through suitable wired or wireless communication configurations to provide signals representative of the pH of the wound fluid for readout, display, etc. at the therapy unit. According to other embodiments, sensor 100 may communicate with other suitable devices to provide the desired pH information of the wound fluid, such as meters, monitors, smartphones, etc. According to other embodiments, the wound dressing and NPWT therapy system may include other components, or omit recited components, as needed to suit a particular wound treatment strategy, and the sensor 100 may be disposed at any appropriate location within the dressing to expose the first electrode to the wound fluid to obtain a desired pH indication.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the terms "exemplary" and "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "first end", "second end", "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A sensor for measuring a pH level in a wound therapy system, the sensor comprising:

a circuit configured to measure a pH level of a wound fluid from a wound area, the circuit comprising:

a substrate having a first end and an opposite second end;

a first electrode printed on the first end of the substrate and comprising a material having a changeable conductivity that changes according to a hydrogen ion concentration level;

a second electrode printed on the first end of the substrate and comprising a material having a fixed conductivity that does not change with the hydrogen ion concentration level;

a porous protective membrane coating covering the first electrode, the porous protective membrane coating comprising a sulfonated and/or carboxylated copolymer and being configured to permit hydrogen ion passage from the wound fluid to the first electrode while preventing direct contact between the wound fluid and the first electrode;

a third electrode printed on the second end of the substrate and being electrically connected to the first electrode via a first electrical trace; and a fourth electrode printed on the second end of the substrate and being electrically connected to the second electrode via a second electrical trace, wherein the circuit measures the pH level by measuring one or more voltage values between the third electrode and the fourth electrode.

2. The sensor of claim 1, wherein the sulfonated and/or carboxylated copolymer comprises a sulfonated tetrafluoroethylene based fluoropolymer-copolymer, and wherein the porous protective membrane coating excludes chitosan.

3. The sensor of claim 2, wherein the porous protective membrane coating comprises tetrafluoroethylene-perfluoro-3,6-dioxa-4-methyl-7-octenesulfonic acid copolymer.

4. The sensor of claim 1, wherein the first electrode and the second electrode are printed in close proximity to each other on the first end of the substrate using screen-printing technology, wherein the first electrode and the second electrode are printed on the same side of the substrate, and wherein the substrate comprises a polymeric material.

5. The sensor of claim 4, wherein the first electrode comprises a carbon-based ink or paste printed on the first end of the substrate and iridium oxide electrodeposited on top of the carbon-based ink or paste.

6. The sensor of claim 4, further comprising a sealing portion formed on a periphery of the first end of the substrate, wherein the sealing portion is an unprinted portion of the substrate and is made of an adhesive material configured to seal the first end of the substrate to one or more components of the wound therapy system.

7. The sensor of claim 4, further comprising an isolation ink layer that separates and protects the first, second, third, and fourth electrodes such that the first and second electrodes can be directly exposed to the wound fluid while the third and fourth electrodes are prevented from being exposed to the wound fluid.

8. The sensor of claim 4, wherein the first electrode has a circular shape, and wherein the second electrode partially surrounds the first electrode.

9. The sensor of claim 1, wherein the first electrode comprises iridium oxide and the second electrode comprises silver chloride.

10. A wound treatment system having a sensor for measuring a pH level of a wound fluid from a wound area, the system comprising:

a wound dressing comprising:

a wound fluid manifold layer overlying the wound area and configured to permit and distribute a flow of wound fluid from the wound area, a drape layer disposed over the wound fluid manifold layer, and a tubing connection pad disposed on and connected to the drape layer;

a negative pressure therapy unit configured to provide a negative pressure at the wound area;

tubing coupling the negative pressure therapy unit to the tubing connection pad; and a sensor configured to measure a pH of the wound fluid from the wound area, the sensor coupled to the tubing connection pad and in fluid communication with the wound fluid from the wound area, the sensor comprising:

a substrate having a first end and an opposite second end;

a first electrode printed on the first end of the substrate and comprising a material having a changeable conductivity that changes according to a hydrogen ion concentration level, the first electrode being covered with a porous protective membrane coating comprising a sulfonated and/or carboxylated copolymer and being configured to permit hydrogen ion passage from the wound fluid to the first electrode while preventing direct contact between the wound fluid and the first electrode;

a second electrode printed on the first end of the substrate and comprising a material having a fixed conductivity that does not change with the hydrogen ion concentration level;

a third electrode printed on the second end of the substrate and being electrically connected to the first electrode via a first electrical trace; and a fourth electrode printed on the second end of the substrate and being electrically connected to the second electrode via a second electrical trace, wherein the sensor measures the pH level by measuring one or more voltage values between the third electrode and the fourth electrode.

11. The system of claim 10, wherein the porous protective membrane coating comprises a sulfonated tetrafluoroethylene based fluoropolymer-copolymer, and wherein the porous protective membrane coating excludes chitosan.

12. The system of claim 10, wherein the porous protective membrane coating comprises tetrafluoroethylene-perfluoro-3,6-dioxa-4-methyl-7-octenesulfonic acid copolymer.

13. The system of claim 10, wherein the first electrode and the second electrode are printed on the first end of the substrate using screen-printing technology, wherein the first electrode and the second electrode are printed on the same side of the substrate, and wherein the substrate comprises a polymeric material.

14. The system of claim 13, further comprising a sealing portion formed on a periphery of the first end of the substrate, wherein the sealing portion is an unprinted portion of the substrate and is made of an adhesive material configured to seal the first end of the substrate to one or more components of the wound therapy system.

15. The system of claim 13, wherein the first electrode is printed on the first end of the substrate with a carbon-based ink or paste, and wherein iridium oxide is electrodeposited on top of the carbon-based ink or paste.

16. A method of fabricating a sensor for measuring a pH level at a wound area, the method comprising:

screen-printing a carbon-based ink or paste on a first end of a substrate comprising a polymeric material;

depositing iridium oxide on the carbon-based ink or paste by electrodeposition to form a first electrode having a changeable conductivity that changes according to a hydrogen ion concentration level;

depositing a porous protective membrane coating on the first electrode wherein the porous protective membrane coating comprises a sulfonated and/or carboxylated copolymer;

screen-printing a second electrode on the first end of the substrate, wherein the second electrode comprises a material having a fixed conductivity that does not change according to a hydrogen ion concentration level;

screen printing a third electrode on an opposite second end of the substrate such that the third electrode is electrically connected to the first electrode via a first electrical trace; and screen printing a fourth electrode on the second end of the substrate such that the fourth electrode is electrically connected to the second electrode via a second electrical trace, wherein the circuit measures the pH level by measuring one or more voltage values between the third electrode and the fourth electrode.

17. The method of claim 16, wherein the porous protective membrane coating is deposited on the first electrode by applying an aqueous solution comprising the sulfonated and/or carboxylated copolymer thereto, wherein the sulfonated and/or carboxylated copolymer comprises about 5% by weight of the aqueous solution.

18. The method of claim 16, wherein the sulfonated and/or carboxylated copolymer comprises tetrafluoroethylene-perfluoro-3,6-dioxa-4-methyl-7-octenesulfonic acid copolymer.

19. The method of claim 16, further comprising curing the aqueous solution using an evaporation process.

* * * * *